United States Patent [19]

Slatkin et al.

[11] Patent Number: 5,339,347
[45] Date of Patent: Aug. 16, 1994

[54] METHOD FOR MICROBEAM RADIATION THERAPY

[75] Inventors: Daniel N. Slatkin, Sound Beach; F. Avraham Dilmanian, Yaphank; Per O. Spanne, Shoreham, all of N.Y.

[73] Assignee: The United States of America as represented by the United States Department of Energy, Washington, D.C.

[21] Appl. No.: 52,927

[22] Filed: Apr. 27, 1993

[51] Int. Cl.⁵ .............................................. A61N 5/10
[52] U.S. Cl. ...................................... 378/65; 378/64; 378/149
[58] Field of Search .................... 378/65, 64, 68, 147, 378/149

[56] References Cited

U.S. PATENT DOCUMENTS

| | | |
|---|---|---|
| 2,139,966 | 12/1938 | Loebell . |
| 2,624,013 | 12/1952 | Marks . |
| 2,638,554 | 5/1953 | Bartow et al. . |
| 3,950,651 | 4/1976 | Flocée . |
| 3,955,089 | 5/1976 | McIntyre et al. . |
| 3,963,935 | 6/1976 | Donnadille . |
| 3,988,153 | 10/1976 | Politycki . |
| 4,140,129 | 2/1979 | Heinz et al. . |
| 4,172,979 | 10/1979 | Morrison . |
| 4,230,129 | 10/1980 | LeVeen ........................... 378/65 X |
| 4,365,341 | 12/1982 | Lam . |
| 4,592,083 | 5/1986 | O'Brien . |
| 4,726,046 | 2/1988 | Nunan . |
| 4,755,685 | 7/1988 | Kawanami et al. . |
| 4,780,898 | 10/1988 | Sundquist ........................ 378/65 |
| 4,827,491 | 5/1989 | Barish . |
| 5,027,818 | 7/1991 | Bova et al. . |
| 5,125,926 | 6/1992 | Rudko et al. . |
| 5,189,687 | 2/1993 | Bova et al. ..................... 378/65 |

FOREIGN PATENT DOCUMENTS 3000439  7/1981  Fed. Rep. of Germany ........ 378/65

OTHER PUBLICATIONS

Slatkin, "Feasibility Study for Microbeam Radiation Therapy with 30–90 keV X-rays from the NSLS X17 Beamline", 37–38 in Ogeka, Ed., *Laboratory Directed Research & Development Program, annual Report to the Department of Energy*, Brookhaven National Laboratory, Upton, N.Y. (1991). (This Publication was made available to the Public on Apr. 27, 1992. See attached letter dated Jan. 20, 1993 from the National Technical Information Service of the Department of Commerce.)

Jones et al., "Biomedical Elemental Analysis and Imaging Using Synchrotron X-Ray Microscopy", *Proceedings of the XIIth Int'l Cong. for Electron Microscopy*, (1990).

Jones et al., "Biomedical Applications of Synchrotron X-Ray Microscopy", *2nd Int'l. Workshop of XRF and PIXE Applications in Life Sciences*, (1989).

Slatkin, et al., "Microbeam Radiation Therapy", *Med. Phys.*, 19, 1395–1400 (1992).

Larsson, "Potentialities of Synchrotron Radiation in Experimental and Clinical Radiation Surgery", *Acta Radiol. Ther. Ph. Biol. Suppl.*, 365, 58–64 (1983).

Leksell, "The Stereotaxic Method and Radiosurgery of the Brain", *Acta Chirugica Scandinavica*, 102, 316–319 (1951).

Ordy et al., "Long-Term Pathologic and Behavioral Changes in Mice after Focal Deuteron Irradiation of the Brain", *Radiation Research*, 20, 30–42 (1963).

*Primary Examiner*—David P. Porta
*Attorney, Agent, or Firm*—David Pascarella; Thomas G. Anderson; William R. Moser

[57] ABSTRACT

A method of performing radiation therapy on a patient, involving exposing a target, usually a tumor, to a therapeutic dose of high energy electromagnetic radiation, preferably X-ray radiation, in the form of at least two non-overlapping microbeams of radiation, each microbeam having a width of less than about 1 millimeter. Target tissue exposed to the microbeams receives a radiation dose during the exposure that exceeds the maximum dose that such tissue can survive. Non-target tissue between the microbeams receives a dose of radiation below the threshold amount of radiation that can be survived by the tissue, and thereby permits the non-target tissue to regenerate. The microbeams may be directed at the target from one direction, or from more than one direction in which case the microbeams overlap within the target tissue enhancing the lethal effect of the irradiation while sparing the surrounding healthy tissue.

44 Claims, No Drawings

METHOD FOR MICROBEAM RADIATION THERAPY

This invention was made with U.S. Government support under Contract Number DE AC02-76CH00016 between the U.S. Department of Energy and Associated Universities, Inc. The U.S. Government has certain rights in the invention.

BACKGROUND OF THE INVENTION

1. Field of the Invention

The present invention is related to methods for performing radiation therapy for cancer treatment. More particularly, the invention relates to methods of using arrays of small radiation beams to irradiate tumors.

2. Background of the Related Art

Cancer continues to be one of the foremost health problems. Conventional treatments such as surgery and chemotherapy have been extremely successful in certain cases; in other instances, much less so. Radiation therapy has also exhibited favorable results in many cases, while failing to be completely satisfactory and effective in all instances. A much less familiar alternative form of radiation therapy, known as microbeam radiation therapy (MRT), is being investigated to treat certain tumors for which the conventional methods have been ineffective.

MRT differs from conventional radiation therapy by employing beams of radiation that are one order of magnitude smaller in diameter than the smallest radiation beams currently in clinical use. The diameter of the microbeams is dependent upon the capacity of tissue surrounding a beam path to support the recovery of the tissue injured by the beam. It has been found that certain types of cells, notably endothelial cells lining blood vessels, have the capacity to migrate over microscopic distances, infiltrating tissue damaged by radiation and reducing tissue necrosis in the beam path. In MRT, sufficient unirradiated or minimally irradiated microscopic zones remain in the normal tissue, through which the microbeams pass, to allow efficient repair of irradiation-damaged tissue. As a result, MRT is fundamentally different from other forms of radiation therapy.

In conventional forms of radiation therapy, including the radiosurgical techniques employing multiple convergent beams of gamma radiation described by Larsson "Potentialities of Synchrotron Radiation in Experimental and Clinical Radiation Surgery," *Acta Radiol Ther. Ph. Biol. Suppl.*, 365, 58–64 (1983), each beam is at least several millimeters in diameter, so that the biological advantage of rapid repair by migrating or proliferating endothelial cells is minimal or nonexistent. As described in greater detail below, our observations of the regeneration of blood vessels following MRT indicate that endothelial cells cannot efficiently regenerate damaged blood vessels over distances on the order of thousands of micrometers ($\mu m$). Thus, in view of this knowledge concerning radiation pathology of normal blood vessels, the skilled artisan would optimally select microbeams as small as 50 $\mu m$ to 200 $\mu m$ in diameter.

The division of a radiation beam into microbeams, and the use of a patient exposure plan that provides non-overlapping beams in the tissue surrounding the target tumor. This allows the non-target tissue to recover from the radiation injury by migration of regenerating endothelial cells of the small blood vessels to the areas in which the endothelial cells have been injured beyond recovery. Therefore, the probability of radiation-induced coagulative necrosis in normal, non-targeted tissue is lowered, which should improve the effectiveness of clinical radiation therapy for deep-seated tumors. The use of microbeams should be of special benefit for deep pulmonary, bronchial, and esophageal tumors, for example, where the effectiveness of orthodox radiation therapy is limited by the risk of radiation pneumonitis.

Effects on the mouse brain of 22 MeV deuterons delivered in a beam having either a circular cross-section (herein designated a "cylindrical" beam) 25 $\mu m$ in diameter or an elongated rectangular cross-section (herein designated a "planar" beam) 25 $\mu m$ in width were investigated 3 decades ago. Representative investigations are described by Ordy et al., "Long-Term Pathologic and Behavioral Changes in Mice After Focal Deuteron Irradiation of the Brain", *Radiation Research* 20, 30–42 (1963). The Ordy et al. publication describes the effects of exposure to high energy deuteron microbeams having a 9 mm ×0.025 mm planar configuration. These beams of heavy charged particles were used in experiments to model the neurological effects of extraterrestrial heavy ions on humans. Ordy et al. do not discuss the treatment of tumors by X-ray microbeam irradiation.

Damage to the cerebrum and cerebellum caused by the deuteron microbeam, was not evident unless a very high radiation dose was given. A macroscopic (1 mm diameter) 22 MeV deuteron beam that delivered about 150–300 Gray (Gy) to the mouse cerebrum caused tissue necrosis in its path. On the other hand, energies of at least 3000 Gy to the cerebral cortex or 720 Gy to the cerebellar cortex were required to leave any persistent brain damage in the path of a 22 MeV, 25- to 40-$\mu m$-wide cylindrical or planar deuteron microbeam, as observed by light microscopy up to 9 months after irradiation. Furthermore, damage was limited to cellular necrosis. Tissue necrosis in the microbeam-damaged zone of the mouse brain was apparently averted by regeneration of blood vessels, even after an absorbed dose of 10,000 Gy or more in the path of the microbeam. Any vascular or parenchymal cell in the microbeam that had been so intensely irradiated was probably destroyed. Cellular necrosis caused by the deuteron microbeam depended mainly on the absorbed dose rather than on the absorbed dose rate, which was varied from 2 to 9,000 Gy $s^{-1}$.

These unprecedented dose-effect relationships in the brain were attributed to the narrowness of the beams and to the regeneration of blood vessels in tissues within the path of the microbeam from the microscopically contiguous, minimally irradiated vasculature adjacent to that path. Presumably, minimally irradiated blood vessels contained reservoirs of endothelium from which regenerating endothelial cells grew into the nearby, maximally irradiated blood vessel segments as the endothelial cells of the latter segments died and disintegrated.

A microbeam tissue-sparing effect was also observed for X-ray microbeams by Straile and Chase, in "The Use of Elongate Microbeams of X-Rays for Simulating the Effects of Cosmic Rays on Tissues: A Study of Wound Healing and Hair Follicle Regeneration", *Radiation Research*, 18, 65–75 (1963). This publication describes the irradiation of mouse skin using a 200 kVp, 0.5 mm Cu+1.0 mm Al-filtered X-ray source. Absorbed doses of about 60 Gy produced a variety of skin lesions when delivered in a seamless (i.e., not spatially interrupted) 5 mm diameter beam. However, much less severe damage occurred when similar doses were delivered to the skin via a 150 $\mu$m wide microbeam. These investigators were primarily concerned with modelling the effects of cosmic rays, and did not describe or suggest the use of microbeams for any therapeutic purposes.

A publication by L. Leksell, "The Sterotaxic Method and Radiosurgery of the Brain," *Acta Chirugica Scandinavia*, 102, 316-319 (1951), describes a stereotaxic instrument suitable for cross-firing radiation treatment of brain tumors. The Leksell publication does not describe the use of microbeams or of multiple simultaneous beams. A related publication by B. Larsson entitled "Potentialities of Synchrotron Radiation in Experimental and Clinical Radiation Surgery," *Acta Radiol. Ther. Ph. Bios. Suppl.*, 365, 58-64 (1983), which further describes the stereotaxic method of Leksell. In addition, Larsson describes a hemispherical helmet-like apparatus for gamma radiation of intracranial targets by multiple converging channels. Larsson does not, however, discuss microbeams or any method of producing microbeams.

U.S. Pat. No. 2,638,554 to Bartow et al. describes various collimators for X-rays which produce a conically converging array of very small beams. One of the collimators described by Bartow et al. is a truncated cone of X-ray-impermeable material cast around a removable array of wires. Once the wires are removed, an array of apertures remains in the collimator which, when inserted into a beam of X-rays, will produce a convergent array of very small beams. The apertures are described as being in the range of 0.25 inches (6.4 mm) to 0.001 inches (25.6 $\mu$m). Another lens described by Bartow et al. is an arcuate lens assembled from planar segments into which grooves have been cut so that when assembled each of the isofocused grooves defines an X-ray transmissive aperture. Neither of the Bartow et al. collimators produces planar beams.

The Bartow et al. patent describes avoidance of excessive concentration of X-rays at any particular spot on the subject skin or tissues by virtue of the discretely spaced small beams. The Bartow et al. patent also describes the rotational or translational movement of the emitting device to produce a cross-firing effect. The Bartow et al. patent does not, however, present any description of a tissue sparing effect at a microscopic level that might be attributable to the specific use of microbeams, positioned to produce just such an effect. Neither do Bartow et al. describe the use of parallel microbeams or the efficacy of the treatment of tumors using parallel microbeams without any converging or cross-firing effect.

U.S. Pat. No. 4,827,491 to Barish also describes accelerator beam collimators having at least one radiation transmission channel. The beams produced by the Barish collimator are generally convergent toward a predetermined target, and range in diameter from about 3 mm to about 4 mm. The Barish collimators are described as useful for the radiation treatment of intra-cranial tumors, but may be applied to treatment of other portions of the body. The Barish patent does not describe microbeams or their utility.

U.S. Pat. No. 2,624,013 to Marks describes a radiation barrier or collimator producing a plurality of relatively large, parallel, rectangular beams. The beams range in size from 0.25 inch to 1 inch on each side. The Marks patent describes the protection of skin by limiting the irradiation of the skin to areas between the beams, thereby helping to retain the skin's integrity. The internal efficacy of the radiation beams produced by the Marks invention is described as relying on recoil electrons to destroy internal tumors. The Marks patent does not describe converging beams or the use of microbeams.

U.S. Pat. No. 4,726,046 to Nunan describes a method and apparatus for generating a relatively small (0.5 mm $\times 0.5$ mm) radiation beam. The Nunan method employs a plan for producing an array of radiation exposures by sequentially scanning over a prescribed area and intermittently delivering radiation beams, but does not describe microbeams.

U.S. Pat. No. 2,139,966 to Loebell describes an X-ray apparatus designed to emit a plurality of convergent X-rays for the treatment of internal disorders. The Loebell apparatus employs several independently movable, X-ray emitting cathode/anode pairs, preferably arranged radially arranged to produce a converging array of beams. The Loebell apparatus is described as capable of eliminating the burning of skin area by the use of converging beams. The Loebell patent does not describe the use of microbeams.

U.S. Pat. No. 4,592,083 to O'Brien describes a rotating shutter for radiation beams. The high speed actuator for controlling the shutter eliminates transition time during which the X-ray dose is wasted. Also describing a beam shutter is U.S. Pat. No. 3,963,935 to Donnadille. This shutter is described as useful for limiting the entry of radiation beams from particle accelerators into irradiation rooms. Neither of these patents describes the use of either single or arrayed microbeams for radiation treatment of tumors.

U.S. Pat. No. 5,125,926 to Rudko et al. describes a system for synchronizing the pulsation of a surgical laser with the heartbeat of a patient undergoing laser heart surgery. The Rudko et al. patent does not describe the synchronization of radiation beams for cancer therapy. Rudko et al. also do not describe the use of the synchronization method with tissues other than heart tissue. Furthermore, Rudko et al. do not disclose the synchronization of radiation impulses with other physiomechanical rhythms.

Although other methods and processes are known for radiation therapy, none provides a method for performing radiation therapy while avoiding significant radiation-induced damage to tissues surrounding the target.

Accordingly, it is a purpose of the present invention to provide a method for treating cancerous tumors by using extremely small radiation microbeams increasing the precision and accuracy of radiation therapy.

It is also a purpose of the present invention to provide a method of using extremely small microbeams of radiation to unexpectedly produce effective radiation therapy.

It is a further purpose of the present invention to provide an improved method of radiation therapy unexpectedly capable of avoiding significant radiation-induced damage to non-target tissues.

Other purposes and advantages of the present invention will be more fully apparent from the ensuing disclosure and appended claims.

SUMMARY OF THE INVENTION

These and other purposes are achieved by the present invention which solves the disadvantages inherent in the prior art by providing a method for performing microbeam radiation therapy (MRT), a specialized technique related to stereotactic radiosurgery.

In contrast to general stereotactic radiosurgery, MRT radiation microbeams having extremely small widths (<500 μm), to irradiate a target, generally a tumor. In MRT, parallel or nearly parallel X-rays are delivered to the target as a spatially fractionated (i.e., microscopically segmented) radiation field, containing a number of microbeams, each microbeam typically being between about 20 μm and about 200 μm wide. Interstitial zones of relatively unirradiated tissue remain between the areas of tissue through which the microbeams pass. These unirradiated zones are typically about 50 μm to about 500 μm wide, depending on the width of microbeams and on other irradiation parameters such as beam energy, dose, and geometry. The beam energies can range from about 30 to several hundred keV.

The method of the present invention employs radiation fields having any of a variety of geometrical configurations. A preferred geometrical option is to employ a linear array of substantially parallel planar microbeams (i.e. microbeams having greatly elongated rectangular cross-sections). While the narrow side of each beam cross-section typically measures between about 20 μm and about 150 μm, the wide side may be as large as in the range of several millimeters to several centimeters. The bundle of microbeams can therefore include substantially parallel, non-overlapping, planar beams with center-to-center spacing of from about 50 μm to about 500 μm, or converging planar beams intersecting at or near the isocenter of the target.

Another geometrical option is a 2-dimensional array of substantially parallel or converging, radially symmetrical, microbeams (e.g., with circular cross-section), having diameters of from about 20 μm to about 200 μm and center-to-center spacing of from about 50 μm to about 500 μm.

Irrespective of whether planar or cylindrical beams are employed, the patient exposure can be performed either unidirectionally (i.e., by exposure of the target using an array of microbeams having one general direction), or from multiple directions allowing the beams to intersect at the isocenter (i.e., the "cross firing" option). These options are also available independently of whether the microbeams in any one array are parallel of convergent.

A major benefit of MRT is that the microbeams are so narrow that the vasculature of the tissue through which the microbeams pass can repair itself by the infiltration of endothelial cells from surrounding unirradiated tissue. Present knowledge indicates that such infiltration can take place only over distances on the order of less than 500 μm depending on the tissue being irradiated. The dimensions of the microbeams and the configuration of the microbeam array are therefore determinable with reference to the susceptibility of the target tissue and the surrounding tissue to irradiation and the capacities of the various involved tissues to regenerate.

Another aspect of the present invention is that the microbeam radiation therapy may be conducted in a pulsed mode. The pulses may be synchronized with either the cardiac or the respiratory cycle or both. Each pulse is limited to a small time interval during the appropriate cycle to avoid the smearing of the extraordinarily precise microbeam effect by movement of the tissue generated by cardiogenic and respiratory pulsation.

For a better understanding of the present invention reference is made to the following description, the scope of which is pointed out in the claims.

DETAILED DESCRIPTION OF THE INVENTION

In microbeam radiation therapy, radiation is delivered to a clinical target, usually a cancerous tumor, as a spatially fractionated field containing a number of microbeams. The field or array of microbeams is generally described with reference to the geometrical arrangement of the microbeams as they pass through an imaginary plane perpendicular to the path of the microbeams. The microbeams do not overlap unless they are at the target volume. Accordingly, the field will comprise areas of high radiation intensity corresponding to the beam cross-sections, as well as areas through which the beams do not pass having relatively low radiation intensity at the interbeam spaces.

MRT in accordance with the present invention may be performed unidirectionally or from more than one direction. Our recent studies have unexpectedly indicated that multiple, parallel planar microbeams, directed at tumors in rat brains from only one direction can result in significant tumor growth control (see Examples 1 and 2). Alternatively, in accordance with previous studies of cross-firing of radiation, it is believed that irradiation of tumors by multiple, angularly displaced, isocentric bundles of microbeams can be efficacious in controlling tumor growth rate (see Example 3).

In observing the known tissue sparing of 22 MeV deuteron microbeams in the mouse brain and exemplary Monte Carlo computations, we inferred that endothelial cells in the brain which are lethally irradiated by any microbeam in an array of adequately spaced microbeams outside an isocentric target are replaced by endothelial cells regenerated from microscopically contiguous, minimally irradiated endothelium in intermicrobeam segments of brain vasculature. Endothelial regeneration mitigates necrosis of the nontargeted parenchymal tissue. However, it is believed neoplastic and/or nonneoplastic targeted tissues at the isocenter are so severely depleted of potentially mitotic endothelial and parenchymal cells by multiple overlapping microbeams that necrosis ensues.

Types of radiation useful for the present invention include, high energy electromagnetic radiation, such as X-ray or gamma radiation. Most preferably the radiation is X-ray radiation. In any generated photon beam, the photons are produced having a characteristic spectrum of energies. The photon energy of the beams useful in the present invention is in the range of from about 30 key to about 300 keV. Most preferably, the energy of the beam is in the range of from about 50 keV to about 150 keV.

Recently, a synchrotron-generated X-ray beam has become available, having practically no divergence and a very high fluence rate. These synchrotron generated X-rays have the potential for projecting sharply defined beam edges deep in the body. This source appears to be potentially useful for generating X-ray microbeams for radiobiology, radiotherapy, and radiosurgery. A high fluence rate is required to implement microbeam radiation therapy (MRT) or microbeam radiosurgery since exposure times must be short enough (e.g., less than about 1 second) to avoid the blurring of margins of the irradiated zones of tissue due to body or organ movements. Sharply defined microbeam margins are made possible not only by the high fluence rate and the minimal divergence of the synchrotron beam, but also by the microscopically short ranges in tissue of secondary electrons (Compton scattering) generated by 50–150 key synchrotron X-rays. Absorbed doses to nontargeted tissues situated between microbeams can be kept below the threshold for radiation damage in tissues both proximal and distal to the isocentric target, i.e., where the microbeams do not overlap. These factors make it possible to effectively irradiate a target using a field of many well defined, closely spaced microbeams.

The radiation beam for producing the microbeam array may be obtained from industrial X-ray generators or, more preferably, from synchrotron beamlines at electron storage rings. Most preferably, the radiation beam is obtained from a wiggler beam line at an electron storage ring. An exemplary beam source is the superconducting wiggler insertion device of the X17B beamline of the National Synchrotron Light Source. A conventional "planar" wiggler uses periodic transverse magnetic fields to produce a beam of rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam.

Synchrotron radiation is linearly polarized in the plane perpendicular to the direction of the magnetic fields generated by the wiggler. For most conventional planar wigglers, these fields are vertical, and the polarization is therefore in the horizontal plane. Since Compton scattering is lower in the direction of the polarization vector, horizontal beam polarization reduces scattering between the microbeams.

By lowering the scattering incident to the beam, the beam profile remains better defined, retaining a small penumbra, i.e., a sharper beam intensity fall-off, as it passes through tissue. The penumbra of the beam is the region at the periphery of the beam where the dose falls rapidly as a function of increasing distance from the center of the beam, measured perpendicularly to the beam axis at a given position along the beam path. The advantage of a small penumbra for X-ray fields is that it permits the protection of nearby radiation-sensitive organs. This protection is particularly pertinent to MRT, since the extraordinarily narrow microbeams and interbeam spacing must be precisely defined to take advantage of the capacity of brain tissue to recover over very small distances. In MRT, a large beam penumbra or shallow fall-off will vitiate the biological advantage of microscopic tissue regeneration by producing more beam overlap within the array.

The dose fall-off at the edge of any individual microbeam inside an array is preferably sharp enough at beam energies of between about 50 keV and about 300 keV, and at tissue depths of from about 1 cm to about 40 cm, to result in large "peak-to-valley" dose ratios (i.e., large ratios of the dose inside the geometrical envelope of a single microbeam to the doses between adjacent microbeams). Such large ratios allow dose planning so that the peak dose will be lethal to most dividing cells, while valley doses will be low enough to allow most normal cells to survive the radiation. The microbeam envelope is defined as the area through which a microbeam, or one or more than one microbeam pulses pass, and in which the absorbed dose of radiation will be lethal to the tissue.

The appropriate selection of the parameters of microbeam field configuration and peak dose is critical to the efficacy of microbeam radiation therapy. The peak dose along the microbeam axis and the center-to-center spacings of the microbeam envelopes must be appropriately selected to insure sufficiently low doses to tissue present in the valleys between the microbeams. The implemented combination of dose and configuration allows endothelial cells, oligodendrocytes (in brain tissue), and perhaps some other cells between the microbeams to divide and to repopulate tissues injured or ablated by the radiation treatment. Thus, unidirectional exposure does not permanently damage normal tissue, and the transient damage to some potentially mitotic cells does not affect the organism. By contrast, multiple exposure of the target at a cross-firing isocenter, irradiating the target volume without microscopic or macroscopic spatial interruption, causes irreparable damage to virtually all blood vessels and other structures within the target tissue. Such multiple irradiation of the target results in enhanced therapeutic necrosis of the target tissue.

Our observations of blood vessel regeneration indicate that endothelial cells cannot efficiently regenerate damaged blood vessels over distances on the order of thousands of micrometers ($\mu$m). In view of the known radiation pathology of normal blood vessels, the skilled artisan would optimally select microbeams as small as 50 $\mu$m to 200 $\mu$m in diameter. Therefore, microbeams useful for the present invention must have cross-sectional configurations such that substantially all non-target tissue within the microbeam envelope will be within the range of the migrating regenerating cells of the particular tissue. As a result, preferred microbeams are regular in cross-section, having a symmetrical geometry. Most preferred geometries include rectangular cross-sections, (bilateral symmetry) as well as radially symmetrical cross-sections such as circular or regular polygonal cross-sections.

The microbeams must have at least one cross-sectional dimension less than about 1 millimeter. Preferably, this dimension is between about 10 micrometers and about 500 micrometers. Most preferably the appropriate cross-sectional dimension is between about 20 micrometers and about 200 micrometers. For example, a preferred rectangular microbeam cross-section would have a short side of about 100 micrometers and another arbitrarily long side, on the order of several millimeters to several centimeters. In such a case the cross-section may be traversed by migrating cells at all points because of the symmetry of the rectangular cross-section and the small width of the rectangle.

Microbeam radiation therapy performed in accordance with the present invention employs at least two spatially distinct microbeams. Preferably, many more microbeams may be used. Generally, since a tumor is macroscopic, having dimensions in the range of millimeters to centimeters, several hundred or several thousand microbeams will be employed. When a group of microbeams are directed at a target from a single direction, the paths traversed by the microbeams may be described as a bundle. Within any bundle the microbeams may converge or diverge, but are preferably substantially mutually parallel. When viewed in cross-section, a microbeam bundle will present an array of individual microbeam cross-sections. Preferably these cross sections do not overlap.

The microbeam arrays useful in the present invention may be linear, rectangular, or otherwise regular in geometry. The linear array is the most preferred option when rectangular microbeams are employed. Specifically, a regular linear array of identical rectangular microbeam envelopes is preferably formed so that the beams are oriented with their long sides substantially parallel to one another. Preferably the microbeams in a linear array are oriented so that their long cross-sectional dimension is substantially vertical relative to gravity. In the preferred linear array, the envelopes in cross-section appear to stand on end in an even row, separated by interbeam spaces. Such an array takes advantage of the inherently low scattering produced by the horizontal beam polarization generated by conventional planar wiggler sources. The planar microbeams preferably have a short dimension within the preferred range of microbeam widths. However, since planar microbeams allow tissue migration along this dimension, the longer dimension may be arbitrarily long, on the order of several millimeters to several centimeters.

Alternatively, the array may be rectangular, or otherwise 2-dimensionally regular. In a rectangular array, for example, the microbeam envleopes may be arranged to form regular columns and rows, each microbeam separated from the others by regular interbeam spaces. A rectangular or other 2-dimensional array is preferred when the envelopes are circular, square, or otherwise substantially radially symmetrical in cross-section.

The array may be created sequentially by irradiating a target with one or a small number of microbeams and then moving the patient in a rectangular translational displacement and irradiating another portion of the target. By a series of horizontal and vertial displacements a relatively large array of microbeams may be created. Stereotactic equipment having microprocessor control is presently within the technical skill of those practicing in the art. Such equipment can manipulate a target with great accuracy and a precision of ±1 micrometer. As a result very highly regular microbeam arrays may be created, taking advantage of the very small dimensons of each microbeam. A sequentially produced array is described in Examples 1 and 2.

Alternatively, the array may be produced simultaneously using a collimator having any of various designs known in the art. Such collimators have multiple radiation transmissive apertures allowing a bundle of regularly spaced microbeams to be directed at a target, simultaneously, by spatially fractionating a radiation beam having macroscopic cross-sections.

The array must position the envelopes so that they do not significantly overlap each other in non-target tissues. Since the envelopes in any array are preferably identical to one another in cross-section, the envelopes must have a minimum center-to-center spacing greater than the appropriate cross-sectional dimension of any individual envelope. The criterion cross-sectional dimension is the minimum width of a microbeam envelope, measured orthogonally to the beam path. The minimum center-to-center spacing is determined along the same line used to measure the cross-sectional dimension.

The microbeams are preferably spaced over intervals greater than the above-defined minimum interbeam spacing to allow the regeneration of tissue. The interbeam spacing may be empirically chosen to optimize the radiation field, depending upon the histological nature of the tissue being irradiated.

The optimum interbeam spacing in any application is also dependent upon the microbeam dose profile. Microbeams having sharper dose fall-off may be spaced more closely, while microbeams having broader profiles must be spaced more widely to achieve a tissue sparing effect. The spacing between microbeam envelopes is dependent upon microbeam profile. The spacing may be determined by calculating the distance between microbeams necessary for defining a peak-to-valley dose ratio that will enable the necessary regeneration of tissue. The maximum valley dose, i.e., the maximum dose that can be absorbed by interbeam tissue without tissue necrosis, is also dependent upon the histology of the tissue being irradiated, and may be optimized empirically.

The intensity of radiation at any point in the plane orthogonal to the path of a beam of X-rays, defining the dose fall-off, is a power function of the distance from the center of the beam path. The radiation dose to tissue, therefore, does not drop to background levels until significant distances are reached. The MRT technique takes advantage of the inherent resistance of tissue to radiation damage at doses slightly above background radiation levels. The microbeams are positioned at center-to-center distances such that at least some tissue between the beams is exposed to a summed, absorbed dose, that is less than the tissue's survivability threshold. Therefore, even though the radiation field is continuous within the microbeam array, the radiation intensity of the field is variable, and the destructive effect of the field is confined to discrete regions, within the microbeam envelopes. In this manner the field is spatially fractionated. As long as some tissue between the microbeams receives doses below its survivable threshold, the microbeam envelopes in a field are not overlapping.

The minimum center-to-center spacing is the distance at which the minimum dose generated within two adjacent microbeam envelopes exceeds the maximum survivable dose for the tissue. The preferred center-to-center spacing, as a result, must be greater than the minimum center-to-center spacing, allowing the minimum dose created by the adjacent microbeams to fall below the threshold survivable dose.

To achieve maximum irradiation of tissue within the microbeam field, the microbeam envelope center-to-center spacing must be minimized without compromising tissue sparing. At the same time the cross-sectional dimensions of the envelopes must be maximized, also without exceeding the limits of cellular migration that is characteristic of the tissue. As mentioned previously, the cross-sectional area of an envelope is defined as the region within which the microbeam dose intensity exceeds the maximum tolerable dose of the particular tissue. As center-to-center spacing of the envelopes is decreased, beam overlap will increase, thereby increasing the minimum radiation intensity within the field. Since this intensity must not exceed the maximum intensity survivable by the tissue and since the volume of tissue receiving this maximum dose must be sufficient to allow regeneration of non-target tissues, the envelope area must be decreased as center-to-center spacing decreases. It is therefore preferred that the intensity fall-off of the microbeams be very steep. In part, a steep fall-off permits the maximum density of microbeams per unit area of the microbeam field since there is less overlap between the microbeams. As a result, the threshold dose of the tissue in the interbeam spaces (radiation intensity minimum of the field) is not exceeded and tissue sparing is not compromised even at extremely small center-to-center spacing.

The microbeam envelopes are preferably arrayed paraxially, which is defined as substantially mutually parallel. However, the microbeams may be generated so as they pass toward the target, they diverge from one another or converge to an isocenter. If the microbeams are not arrayed paraxially then it is preferred that the microbeams are spaced at intervals sufficient to avoid irreparable damage to normal tissues at any point along their paths. If the microbeams are convergent it is preferred that the valley dose of the field not exceed the maximum dose tolerated by the non-target tissue until at or near the limits of the target volume. More particularly, the maximum tolerated dose should not be exceeded in tissue proximal or distal to the target volume. The convergent microbeam envelopes should not overlap except within the target volume.

Similar considerations apply to the choice of angles when MRT is performed in the cross-firing mode in accordance with the present invention. In the cross-firing mode, the angular displacement of the microbeam bundles must be sufficient to ensure that the maximum tolerated dose is not exceeded in tissues proximal and distal to the target volume. By the same token, each microbeam bundle must be angularly displaced sufficiently from the others to ensure that the arrays do not overlap except at regions close to or within the target volume.

When parallel, cylindrical 25 $\mu$m diameter microbeams are spaced at 200 $\mu$m intervals, only about 1.2% of the tissue enclosed by the outer envelope of the microbeam array is directly irradiated. The majority of the tissue remains unirradiated. It is more difficult, therefore, to achieve major geometrical irradiation coverage of a clinically significant target by crossfired bundles of parallel cylindrical microbeams. Thus, for MRT, arrays of cylindrical or other radially symmetrical microbeams would not be preferred unless the microbeams were non-parallel, converging toward the target.

On the other hand, a bundle of parallel, 25 $\mu$m wide planar microbeams spaced at 200 $\mu$m center-to-center intervals, provides much more irradiation coverage, i.e., about 12.5%, than the array of cylindrical microbeams described above, yet such a bundle of planar microbeams is estimated to provide nearly as much tissue sparing. This unexpectedly beneficial result is due to the much smaller peak-to-valley absorbed dose ratios characteristic of the array of planar microbeams.

The efficacy of MRT is in part a function of the extraordinary precision of the beam spacing and the extraordinary narrowness of the microbeams themselves. Should the microbeam effect be smeared by movement of the surrounding tissue into the path of the beams, the benefit gained by the extreme narrowness of the beams would be attenuated, if not vitiated. Random or intentional macromotion of the patient will cause motion on a comparatively large scale, which can completely negate the tissue sparing effect of MRT. For this reason MRT is most preferably performed in conjunction with stereotactic apparatus to reduce or preferably eliminate such macromotion. However, even when the patient is stereotactically immobilized other sources of tissue motion remain. In particular, tissue micromotion is induced by physiomechanical cycles such as cardiac pulsation and pulmonary or respiratory cycles. MRT is therefore preferably performed in a pulsed mode, the pulsations of the microbeams coinciding with the rhythmic displacements of the target tissue resulting from the relevant physiomechanical rhythms. To limit such smearing the microbeam exposure may be pulsed to intersect with the appropriate tissue segment in harmony with the physiomechanical displacement of the tissue. An electromechanical oscillating shutter or similar device may be used to confine the irradiation period to a particular segment of the cardiac cycle and/or the respiratory cycle, the oscillation frequency varying in response to variations in the cycle frequency.

While MRT according to the present invention may be performed in synchrony with a physiomechanical cycle, it is also possible to perform MRT in a pulsed mode without regard for any physiomechanical cycle. The pulses may have durations ranging from about 20 milliseconds to about 2 seconds, depending on the energy of the X-ray source and the dose desired to be delivered.

In using microbeam radiation therapy to treat brain or spinal cord tumors, the irradiation is most preferably carried out in a pulsed mode. In this mode, the pulses are synchronized with the electrocardiogram. The exposure is limited to a small time interval of the heartbeat period, to avoid the smearing of the microbeam effect by pulsation caused by the cardiogenic pulsation of arteries in and near the brain or spinal cord. The portion of the cardiac contraction cycle selected for pulsed irradiation may be associated with minimum velocity or minimum acceleration of the brain or spinal cord vasculature. Based on our understanding of central nervous system blood circulation, it is believed that the optimal irradiation pulse may be at or near the T wave of the electrocardiogram, during diastole. However, the cardiosynchronous pulsation need not be limited to any specific portion of the cardiac cycle. An electromechanical oscillating shutter or a continuously rotating shutter may be used to confine the irradiation period to any desirable segment of the cardiac cycle. Either the frequency of oscillation of the shutter or the angular velocity of rotation of the shutter may be synchronized with electrocardiograph signals through a computer or microprocessor to effect the desired pulsation of irradiation. In one embodiment, a continuous recording of the electrocardiogram linked to an analog-to-digital converter may be used, so that the electrocardiograph voltage are recorded numerically in computer memory. A compute program would then act to determine the time of maximum voltage during the T-wave. The electromechanical shutter would open within several hundredths of a second after the maximum voltage to allow one pulse of microbeam radiation to the target.

In all immobilized parts of the body, except in those within the thorax and abdomen, the principal motions of tissues are synchronous with the heartbeat. In the thorax and abdomen, however, the principal motions are synchronous with the respiratory cycle. The method of the present invention, therefore, may further comprise the use of radiation pulses in synchrony with either the cardiac or the respiratory cycle, or in part with both cycles. Synchronization would depend on the anatomic site of the target and the complex patterns of physiomechanically cyclic micromotion and macromotion of the target. This aspect of the present invention is particularly important to spare the lung from radiation-induced pneumonitis when irradiating a target deep in the thorax, whether in the lung, the mediastinum, the thoracic paravertebral and vertebral tissues, or the heart itself. In these circumstances, the sparing effect of microbeams may be attributable to sparing of radiation-sensitive epithelial cells that line the alveolar air spaces, as well as the sparing of endothelial cells that line pulmonary blood vessels. MRT may, therefore, be applicable to palliative and possibly curative radiation therapy of lung and esophageal cancers, which are common causes of prolonged illness in elderly patients.

The following examples further illustrate the present invention. In the Examples X-ray radiation generated by a wiggler beam line at a synchrotron was collimated to a rectangular microbeam 30 μm wide. The collimator comprises a circular disk of tantalum 0.5 inches in diameter and 0.25 inches thick that has been cut in half along a diameter and fixed in a frame leaving the two halves of the disk separated by a space of 30 μm through which the microbeam was passed. The height of the X-ray beam was limited by a larger beam aperture so that the microbeam height was 4 mm. The X-ray energy was filtered through a 0.2 mm thick gadolinium filter producing a median beam energy of about 50 keV,. with 90% of the photons having energies between 30 and 130 keV.

Planar microbeams with heights greater than 4 mm were generated in the following manner: After each exposure to a single microbeam, the subject being irradiated was laterally translocated a desired distance by means of a microprocessor controlled stereotactic device. The subject was then irradiated with the microbeam producing the desired dose. The parallel planar microbeams are thereby easily produced in any desired number with any desired center-to-center spacing. By vertically translocating the experimental subject 4 mm and irradiating at positions identical to the first array microbeams 8 mm high were produced. This vertical translocation step was repeated to produce microbeams up to 12 mm in height.

EXAMPLE 1

Our experiments have shown that X-ray irradiation of 30 μm-wide brain slices having 4–16 mm-high, rectangular cross-sections with peak doses up to at least 625 Gy does little or no permanent damage to the normal rat brain when the slices are in multiple (40–80) parallel planes separated at 100–200 μm center-to-center intervals. Monte Carlo computations for an adult human head phantom (Slatkin et al , . "Microbeam Radiation Therapy", *Medical Physics,* 19(6), (1992)) have indicated how one may exploit microbeams for human radiotherapy by using a cross-fire technique with the target tumor at the cross-fire isocenter. Our recent studies of the degree of tumor growth-inhibition provided by multiple, parallel, unidirectional microbeams unexpectedly and very encouragingly resulted in long-term growth control of nearly half of the malignant rat brain tumors treated with one of the two MRT protocols tested. These protocols were developed for microbeam irradiation of a standard 4 mm diameter malignant right frontocerebral rat brain tumor (9L gliosarcoma of the right frontal lobe 14 days after right frontocerebral injection of $10^4$ viable tumor cells suspended in 1 μl of medium). The radiation employed was X-ray radiation generated at a wiggler beam line at a synchrotron. The X-ray radiation had beam energies in the range of 30–130 keV.

Protocol A: 625 Gy incident upon a series of forty parallel 30 μm-wide, 16 mm-high anteroposterior head slices, each narrow slice of directly irradiated head tissue separated from adjacent directly irradiated, virtually parallel slices by 200 μm center-to-center.

Protocol B: 625 Gy incident upon a series of forty parallel 30 μm-wide, 16 mm-high anteroposterior head slices, each directly irradiated slice separated from adjacent directly irradiated, virtually parallel slices by 100 μm center-to-center.

Protocol A resulted in about 70% reduction in clonogenic tumor cell survival. This determination was made through counting those surviving tumor cell clones that had an arbitrary standard minimum rate of growth in vitro. Protocol A also produced a twofold extension of the median postirradiation day of death, from 5 days for seven unirradiated, matched, brain-tumor-bearing control rats, to 10 days for six irradiated tumor-bearing rats.

Protocol B resulted in about 98% reduction of clonogenic tumor cell survival. Protocol B also produced a fourfold extension of the median postirradiation day of death, from 5 days for the control rats, to 20 days for seven irradiated rats. Analysis of the weight changes in these rats together with their post-irradiation survival times using the 'morbidity index' method (Coderre et al., *Radiay Res.,* 128, 177–85, 1991) of non-parametric analysis indicated a highly significant (>99.5% confidence level) palliative effect of Protocol B even with the small numbers of rats used for the study. More remarkable was the 30-fold extension in the lifetimes of the three long-term surviving rats in the 100 μm group, in comparison with the 5-day median life expectancy of the untreated rats. Protocol B animals, five months after irradiation, showed no obvious neurological deficits. Indications of the radiation treatment of malignant brain tumor in these rats included loss of some fur on the right side of the head associated with subacute blepharitis. Four months after radiation, cataract in the right eye was observed in all three survivors. Also, right frontocerebral cystic gliosis was detected by magnetic resonance imaging (MRI) 68 days post-irradiation.

EXAMPLE 2

Further evidence of the palliative effect of unidirectional microbeam radiation therapy was obtained shown by the following experimental investigation of cerebral tumors in rats.

Using a protocol similar to that described in Example 1, 7 rats were given left frontocerebral injections of $10^4$ viable 9L gliosarcoma cells. In this well established protocol, median survival is 20 days ±3 days. At 17.5 days after implantation of the tumor, the tumor normally has advanced to a mass of about 175 mg.

The 7 rats received irradiation according to the following protocol: Each rat was irradiated in an anteroposterior direction using an array of vertical planar microbeams, produced sequentially. Each microbeam was 30 μm wide and 4 mm high. After each exposure, the rat being irradiated was moved 100 μm to one side by a microprocessor controlled stereotactic device, thereby producing 100 μm center-to-center spacing between microbeams. The exposures began at 4 mm to the right of the midline, proceeding to the left side of the animal, ending at 12 mm to the left of the midline. On completion of this series of exposures, the animal was elevated by 4 mm and a second series of exposures was commenced proceeding from the left side to the right side of the animal. Finally a third series of exposures was performed proceeding right to left after the animal was raised an additional 4 mm. Therefore the array of microbeams produced by this protocol was 16 mm wide and 12 mm high.

The rats were divided into two groups according to the peak dose of the microbeams in each arrray. Group I (4 rats) received microbeams having a peak dose of 337.5 Gy, while Group II (3 rats) received microbeams having a peak dose of 225 Gy.

Notwithstanding the extraordinarily late stage of the tumor progression, an unexpected palliative effect was observed as measured by survival of the rats. Rats from Group I exhibited a median survival of 10.5 days post-irradiation, with an average survival of 9.5 days. This is equivalent to a four-fold extension of survival. Rats of Group II showed median survival of 3 days, with an average survival of 6.3 days. Given the stage of tumor progression at the time of irradiation, median survival is expected to be approximately 2.5 days.

EXAMPLE 3

In this example, microbeam radiation therapy in a cross-firing mode was demonstrated by computer modelling the irradiation of a human head phantom with X-ray microbeams fired from several angles. The human head phantom was a 16 cm diameter, 16 cm high cylindrical water target, believed to approximate the size and density of a human head target. Each microbeam bundle was composed of 150 substantailly parallel planar microbeams. Each microbeam was 25 $\mu$m wide and 30 mm high. The center-to-center spacing of the microbeams was 200 $\mu$m. Therefore the microbeam bundles being modelled had cross-sections of 3 cm $\times$ 3 cm.

Using computer codes capable of calculating the scattering of electrons and the dispersion of X-ray radiation, 8 cross-fired bundles of 100 key microbeams were found to produce an estimated >48 Gy average absorbed dose at a 7.5 cm deep target with $\leq$2.9 Gy interbeam absorbed doses at tissue proximal and distal to the target. If it is accepted that the minimum threshold dose for irreversible morphological damage from irradiation of mature mammalian brain is on the order of 10 Gy, the 2.9 Gy interbeam absorbed dose would avoid tissue necrosis in non-targeted zones.

Thus while we have described what are presently the preferred embodiments of the present invention, other and further changes and modifications could be made without departing from the scope of the invention, and its is intended by the inventors to claim all such changes and modifications.

We claim:

1. A method of performing radiation therapy on a patient comprising the step of
   irradiating a target tissue with a therapeutic quantity of high energy electromagnetic radiation from a radiation source through at least two substantially mutually parallel spatially distinct microbeam envelopes, each envelope describing a path having a width less than about i millimeter, wherein the target tissue within the microbeam envelope receives a summed absorbed dose of radiation exceeding a maximum absorbed dose survivable by the target tissue and non-target tissue between adjacent microbeam envelopes receives a summed absorbed dose of radiation less than a minimum absorbed dose lethal to non-target tissue thereby permitting irradiated non-target tissue to regenerate.

2. The method of claim 1, wherein said irradiating further comprises said microbeam envelope path width being between about 10 micrometers and about 500 micrometers.

3. The method of claim 1, wherein said irradiating further comprises said microbeam envelope path width being between about 20 micrometers and about 100 micrometers.

4. The method of claim 1, wherein said irradiating further comprises said microbeam envelope having a rectangular cross-section.

5. The method of claim 4, wherein a side of the rectangular cross-section is from about 20 micrometers to about 100 micrometers.

6. The method of claim 1, wherein said irradiating further comprises said microbeam envelope having a substantially radially symmetrical cross-section.

7. The method of claim 6, wherein the microbeam envelope has a substantially circular cross-section.

8. The method of claim 7, wherein the microbeam envelope cross-section has a diameter of from about 20 micrometers to about 100 micrometers.

9. The method of claim 1, wherein the radiation is monochromatic.

10. The method of claim 1, wherein the radiation is generated by a synchrotron.

11. The method of claim 10, wherein the radiation is generated by a wiggler insertion device.

12. The method of claim 1, wherein said irradiating further comprises generating a microbeam bundle, which has a plurality of spatially distinct microbeam envelopes.

13. The method of claim 12, wherein generating the microbeam bundle comprises generating a substantially regularly spaced array of microbeams envelopes.

14. The method of claim 13, wherein the array is substantially linear.

15. The method of claim 13 wherein the array is 2-dimensional.

16. The method of claim 15 wherein the array is substantially rectangular.

17. The method of claim 15, wherein the array is substantially radially symmetrical.

18. The method of claim 17, wherein the array is substantially circular.

19. The method of claim 12, wherein the microbeam envelopes of said microbeam bundle have a center-to-center spacing of from about 50 micrometers to about 500 micrometers.

20. The method of claim 12, wherein the microbeam bundle envelopes of said microbeam bundle have a center-to-center spacing of from about 50 micrometers to about 200 micrometers.

21. The method of claim 1, wherein the irradiating further comprises producing the microbeams simultaneously.

22. The method of claim 1, wherein the irradiating further comprises producing the microbeams in temporally discrete radiation pulses.

23. The method of claim 12, wherein said irradiating further comprises producing a plurality of microbeam bundles.

24. The method of claim 23, wherein the microbeam bundles are substantially mutually parallel.

25. The method of claim 24, wherein the microbeam bundles are rectangularly translationally displaced from each other and substantially mutually parallel.

26. The method of claim 23, wherein the microbeam bundles are angularly displaced from each other and substantially isofocused and mutually convergent.

27. The method of claim 12, wherein said irradiating further comprises generating each microbeam bundle in a single radiation pulse.

28. The method of claim 12, wherein said irradiating further comprises generating each microbeam bundle by delivering a plurality of temporally discrete radiation pulses.

29. The method of claim 28, wherein said plurality of radiation pulses irradiate the target tissue with substantially identical microbeam envelopes.

30. The method of claim 28, wherein the radiation pulses irradiate said target tissue with rectangularly translationally displaced microbeam envelopes.

31. The method of claim 28, wherein the radiation pulses have substantially regular durations and substantially regular interpulse intervals.

32. The method of claim 31, wherein the radiation pulses have a duration of from about 20 milliseconds to about 2 seconds.

33. The method of claim 31, wherein the radiation pulses have durations and interpulse intervals substantially synchronized with a physiomechanical cycle of the patient.

34. The method of claim 33, wherein the physiomechanical cycle is a cardiac cycle.

35. The method of claim 33, wherein the physiomechanical cycle is a pulmonary cycle.

36. The method of claim 33, wherein the physiomechanical cycle is a cardiopulmonary cycle.

37. The method of claim 1, wherein the radiation is focused.

38. The method of claim 1, wherein the radiation is unfocused.

39. The method of claim 1, wherein the target is a tumor.

40. The method of claim 39, wherein the tumor is intracranial.

41. The method of claim 1, further comprising stereotactically immobilizing the patient.

42. The method of claim 1, wherein the radiation is X-ray radiation.

43. The method of claim 42, wherein the radiation has a beam intensity within a range of from about 30 key to about 300 keV.

44. The method of claim 42, wherein the beam intensity is within a range of from about 50 keV to about 150 keV.

* * * * *